(12) United States Patent
Hennessy

(10) Patent No.: US 8,894,595 B2
(45) Date of Patent: Nov. 25, 2014

(54) TRACTION HIP BRACE

(71) Applicant: Stephen Hennessy, Vancouver, WA (US)

(72) Inventor: Stephen Hennessy, Vancouver, WA (US)

( * ) Notice: Subject to any disclaimer, the term of this patent is extended or adjusted under 35 U.S.C. 154(b) by 175 days.

(21) Appl. No.: 13/730,152

(22) Filed: Dec. 28, 2012

(65) Prior Publication Data

US 2014/0188022 A1    Jul. 3, 2014

(51) Int. Cl.
*A61F 5/00*    (2006.01)

(52) U.S. Cl.
USPC .................. 602/16; 602/23; 602/26; 602/27

(58) Field of Classification Search
USPC ......... 602/5, 16, 23–28; 128/95.1, 96.1, 99.1, 128/882
See application file for complete search history.

(56) References Cited

U.S. PATENT DOCUMENTS

| | | | |
|---|---|---|---|
| 5,419,755 A | 5/1995 | Fukumoto et al. | |
| 5,662,693 A * | 9/1997 | Johnson et al. | 607/49 |
| 5,961,541 A * | 10/1999 | Ferrati | 607/49 |
| 6,210,353 B1 | 4/2001 | Barnes | |
| 7,153,242 B2 * | 12/2006 | Goffer | 482/66 |
| 7,419,253 B2 * | 9/2008 | Olsen et al. | 347/86 |
| 8,171,570 B2 * | 5/2012 | Adarraga | 2/22 |
| 2007/0056592 A1 * | 3/2007 | Angold et al. | 128/845 |
| 2012/0289878 A1 | 11/2012 | Schwenn et al. | |

OTHER PUBLICATIONS

Bledsoe Brace Systems, "Bledsoe Axiom/Axiom-D Custom & OTS Knee Brace Application Instructions & Patient Manual", Jan. 2007, pp. 1-4.

Bledsoe Brace Systems, "Bledsoe Axiom & Axiom-D OTS Functional Knee Brace", 2005, pp. 1-2.
Bledsoe Brace Systems, "Bledsoe Ultimate CI Brace", 2003, pp. 1-2.
Bledsoe Brace Systems, "Bledsoe Axiom Sport / Ultimate CI Brace Application Instructions & Patient Use Manual", Mar. 2007, pp. 1-5.
Bledsoe Brace Systems, "The Changing Face of OA", 2008, pp. 1-2.
Bledsoe Brace Systems, "Ligament Braces", Jan. 2009, pp. 1-4.
Bledsoe Brace Systems, "Bledsoe Ultimate Dynamic Brace Application Instructions", Mar. 2004, pp. 1-6.
Bledsoe Brace Systems, "Bledsoe Extender Brace Application Instructions", Jul. 2002, pp. 1-4.
Bledsoe Brace Systems, "Bledsoe Lever Lock Knee Brace", 2004, pp. 1-2.
Bledsoe Brace Systems, "Bledsoe Lever Lock Brace Application Instructions", Jul. 2002, pp. 1-2.

(Continued)

*Primary Examiner* — Michael A. Brown
(74) *Attorney, Agent, or Firm* — Wong, Cabello, Lutsch, Rutherford & Brucculeri, L.L.P.

(57) ABSTRACT

A traction hip brace which provides a traction force to the femur, pulling it out and away from the acetabulum. A knee brace element secures around the lower thigh and below the knee at the upper shin using two shells with adjustable straps. An articulating hinge allows bending of the knee. A strut member extends from the knee hinge up to a saddle harness. The strut member has an articulating hinge that can be locked to prevent motion if desired. The terminus end of the strut member is inserted into a holster of the saddle harness worn by the user. The saddle harness is fitted to the user's waist and buttock and provides the anchor point for the end of the strut member. Attachment straps are used to tension the strut member down and away from the saddle harness to exert a traction force on the femur.

17 Claims, 5 Drawing Sheets

(56) References Cited

OTHER PUBLICATIONS

Bledsoe Brace Systems, Bledsoe or Brace Application Instructions, Feb. 2007, pp. 1-3.

Bledsoe Brace Systems, "Original Bledsoe Brace Application Instructions", Feb. 2007, pp. 1-5.

Bledsoe Brace Systems, "Bledsoe Simple Pelvic Brace", pp. 1-2, (no date).

Bledsoe Brace Systems, "Bledsoe Pelvic Brace Application Instructions", Apr. 2002, pp. 1-3.

Bledsoe Brace Systems, "Bledsoe Philippon Post-op Hip Brace", 2004, pp. 1-2.

Bledsoe Brace Systems, "Bledsoe Philippon Post-Arthroscopy Hip Brace Application Instructions", Aug. 2007, pp. 1-3.

Bledsoe Brace Systems, "Bledsoe Sport & Sport Max Braces", 2004, pp. 1-2.

Bledsoe Brace Systems, "Sport & Sport Max Standard & Front Closure Application Instructions", Oct. 2007, pp. 1-2.

\* cited by examiner

TRACTION HIP BRACE

BACKGROUND OF THE INVENTION

1. Field of the Invention

The invention relates to braces and orthopedic supports that are strapped to the body to support joints and extremities, and specifically to a brace that is designed to traction the femur away from the hip socket.

2. Description of the Related Art

Orthopedic supports are well established and widely used. Most braces and supports related to the hip are designed as post-operative devices to limit the range of motion of the joint or limb during activities or motions that may stress the joint (Burgess, US Pub. No. 2012/0289878 A1), support the joint during rehabilitation (Fukumoto, U.S. Pat. No. 5,419,755) or provide a lateral force to the joint, pressing the femur into the acetabulum (Barnes, U.S. Pat. No. 6,210,353). It would be desirable to have a brace designed to be employed as a pre-operative device to reduce an individual's pain due to arthritic joint degeneration where the joint space and cushion are damaged and the individual is postponing or awaiting joint replacement surgery.

SUMMARY OF THE INVENTION

A traction hip brace according to the present invention provides a traction force to the femur, pulling it out and away from the acetabulum. A knee brace element secures around the lower thigh and below the knee at the upper shin using two shells with adjustable straps. An articulating hinge allows bending of the knee. The traction hip brace has a strut member that extends from the knee hinge up to a saddle harness. This strut member is adjusted to the desired knee to hip joint dimension of the user. The strut member has an articulating hinge that can be locked to prevent motion if desired. The terminus end of the strut member is inserted into a holster of the saddle harness worn by the user. The saddle harness is fitted to the user's waist and buttock and provides the anchor point for the end of the strut member. Attachment straps are used to tension the strut member down and away from the saddle harness to exert a traction force on the femur.

BRIEF DESCRIPTION OF THE FIGURES

The accompanying drawings, which are incorporated in and constitute a part of this specification, illustrate an implementation of apparatus and methods consistent with the present invention and, together with the detailed description, serve to explain advantages and principles consistent with the invention.

DETAILED DESCRIPTION OF THE PREFERRED EMBODIMENTS

Figure 1:
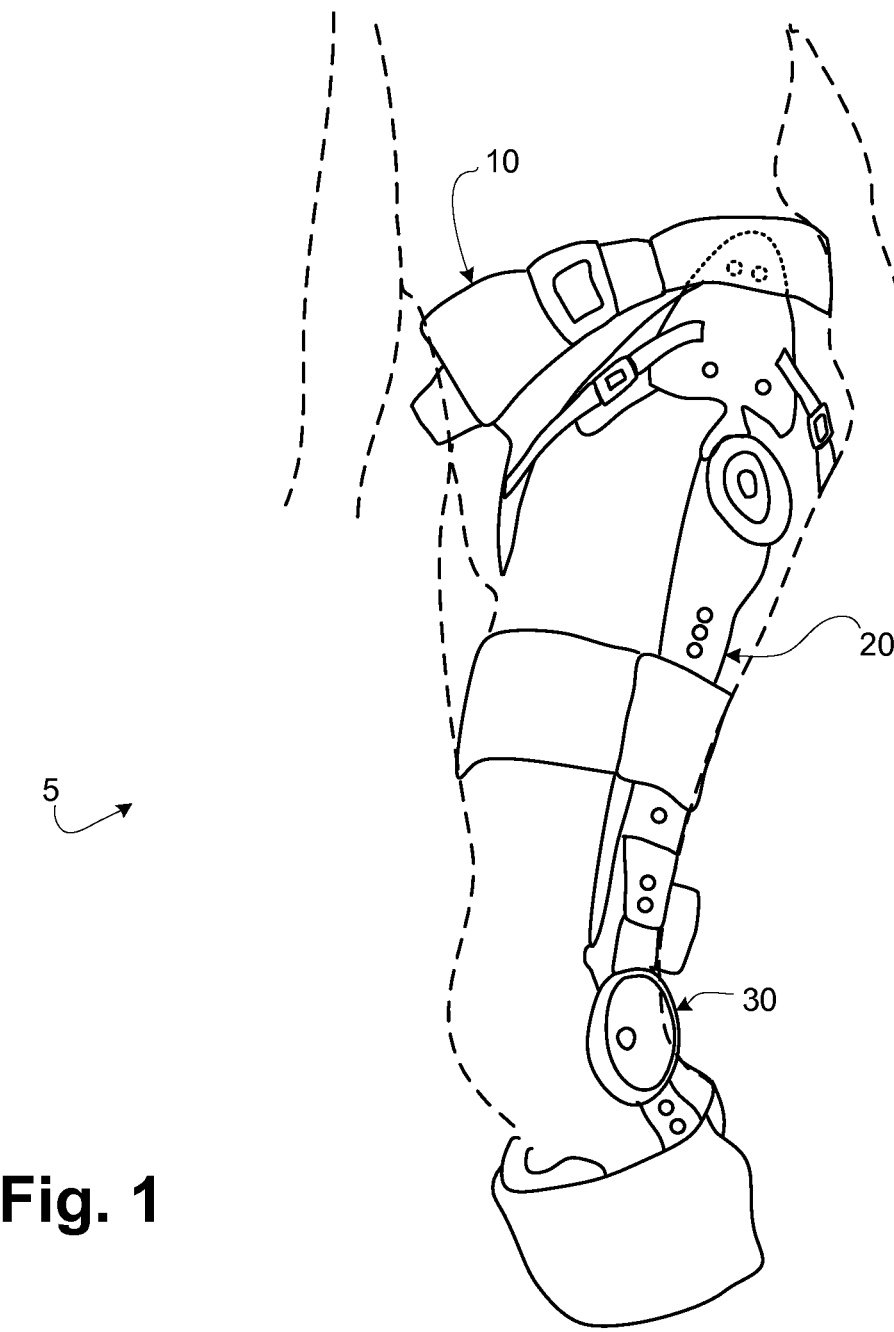
FIG. 1 is an isometric drawing of a traction hip brace according to the present invention.

As illustrated in FIGS. 1-5, the preferred embodiment of a traction hip brace 5 has three major components shown in FIG. 1: a saddle harness 10, a strut member 20 and a knee brace 30. The saddle harness 10 is sized to the individual's waist and buttock with adjustments by straps and buckle attachments in a conventional manner. The strut member 20 and knee brace 30 are adjusted to a desired dimension suited to the individual's knee to hip joint distance. In addition to the knee to hip joint dimension and waist and buttock dimension, other relevant dimensions for sizing the traction hip brace include the circumference of the lower thigh above the knee joint and the circumference of the upper calf below the knee joint.

Figure 2:
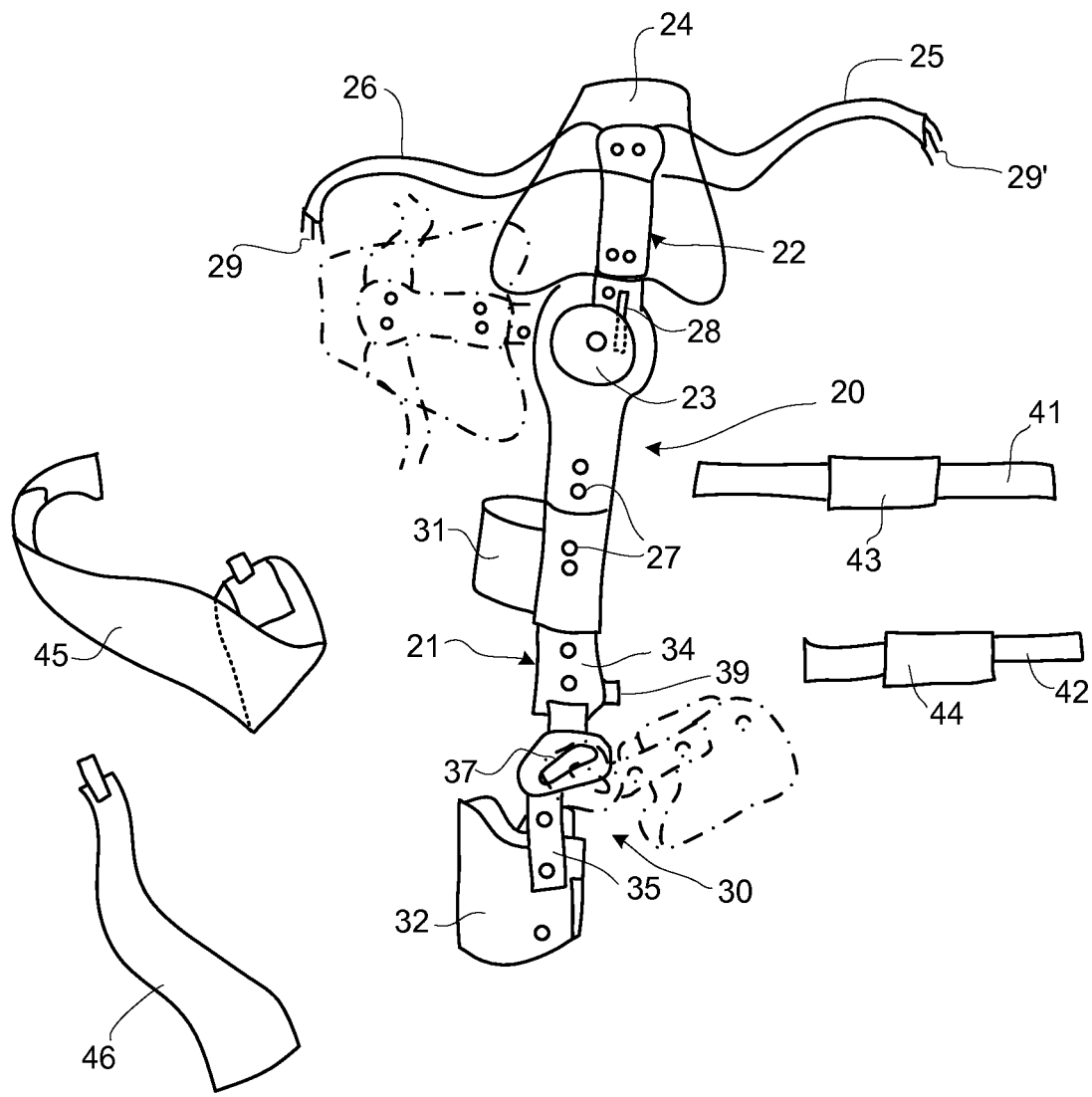
FIG. 2 is a strut member side view of the traction hip brace of FIG. 1.
Figure 4:
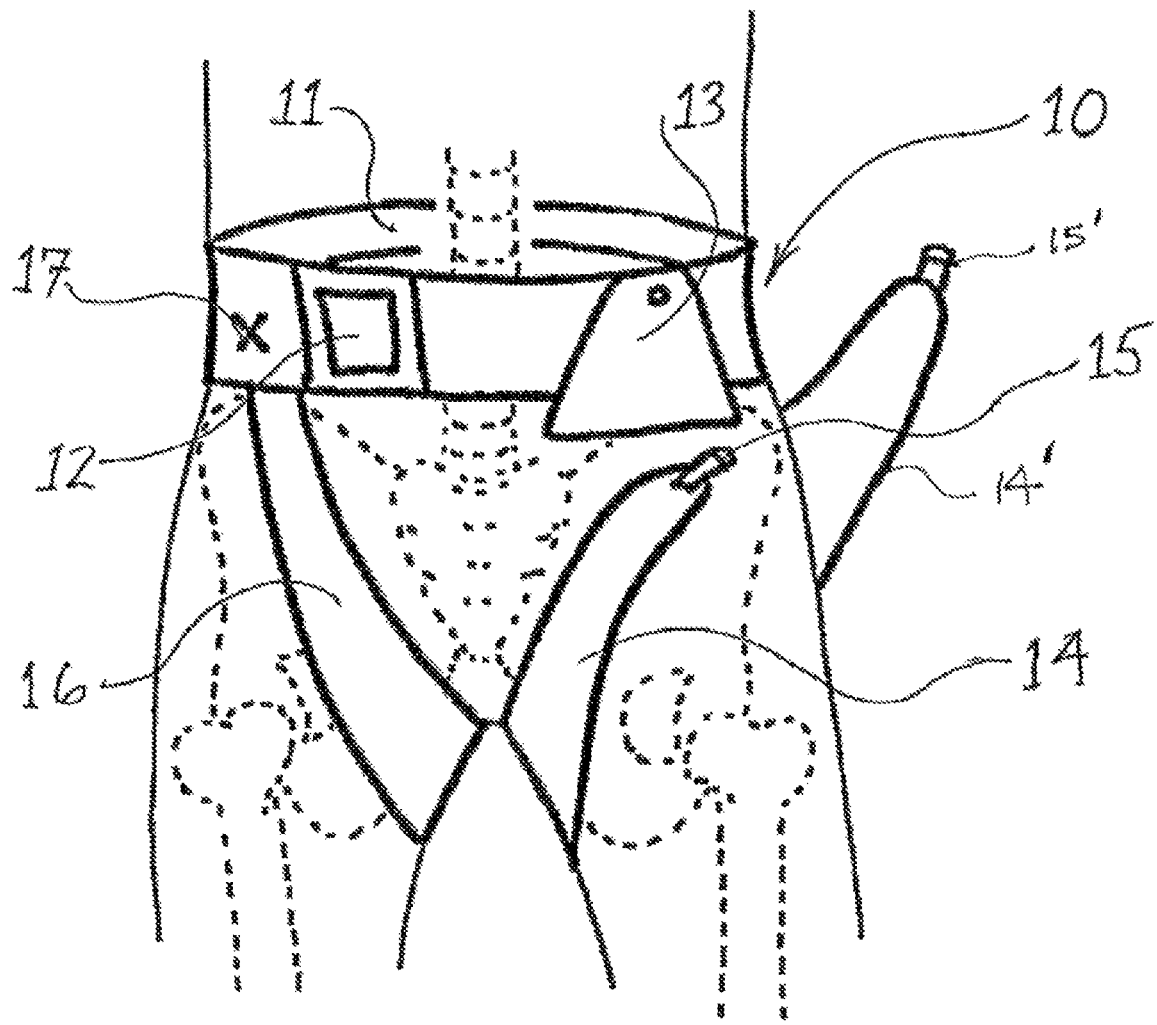
FIG. 4 is a front saddle harness and holster view of the traction hip brace of FIG. 1.
Figure 5:
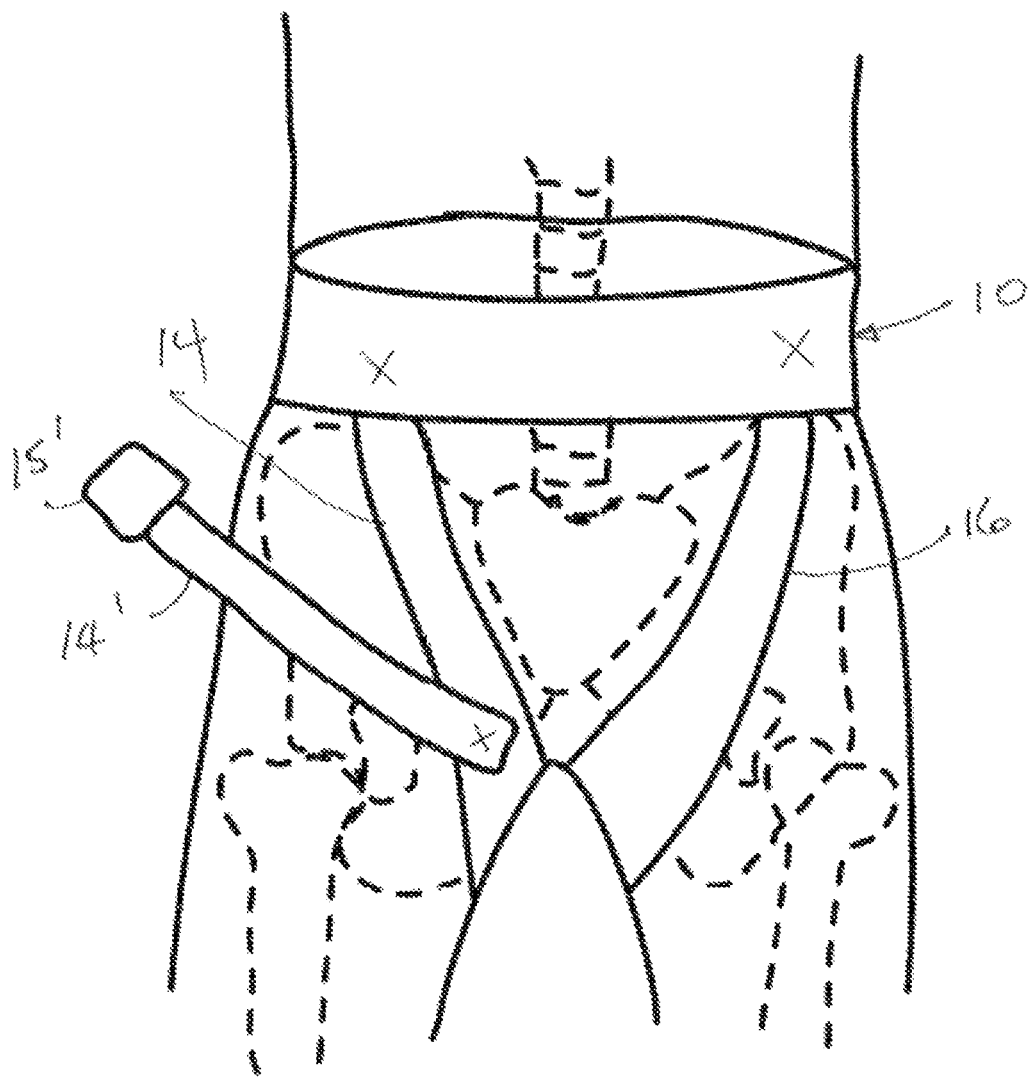
FIG. 5 is a rear saddle harness and holster view of the traction hip brace of FIG. 1.

Referring to FIGS. 4 and 5, the saddle harness 10 of the traction hip brace 5 is preferably an assembly of nylon strapping, reinforced plastic panels, fabrics, natural materials and adjustable buckles 12 with attachments 17. Other materials and arrangements to provide a harness can be used, as commonly done and as apparent to one skilled in the art. The saddle harness 10 is worn by the user and secured tight at the beltline 11, capturing the iliac crest of the hip bone. The saddle harness 10 has a built in holster 13 to accept a spade 24 of the strut member 20 (FIG. 2). The saddle harness 10, as illustrated in FIGS. 4 and 5, has groin straps 14 and 14' on the brace side and strap 16 on the non-brace side.

On the non-brace side the groin strap 16 runs from the rear belt line 11 under the pubic bone of the groin to attachment point 17. The length of the groin strap 16 is adjustable, in one embodiment the groin strap 16 being formed in two pieces that are secured together with hook and loop attachments, allowing adjustment to the individual. Alternatively a loop can be attached at the attachment point 17 and the groin strap 16 can pass through the loop and attach to itself using appropriately placed hook and loop material or a strap adjuster. As another alternative, a cam buckle can be placed at the attachment point 17 and the groin strap 16 passed through the cam buckle and secured. Other methods of fastening the groin strap 16 to the saddle harness 10 and allowing length adjustment can readily be used, as apparent to one skilled in the art.

On the brace side there are several alternate embodiments. The front groin strap 14 attaches to the saddle harness 10 at the rear belt line 11 and passes under the pubic bone to end in a buckle 15. The rear groin strap 14' is secured to the front groin strap 14 at a location in the groin area and extends rearwardly and upwardly to end in a buckle 15'. In a first embodiment the buckles 15 and 15' are secured to the spade 24 of the strut member 20 with front attachment strap 26 and rear attachment strap 25 mounted on the spade 24 and ending in buckles 29 and 29', with buckle 15 mating with buckle 29 and buckle 15' mating with buckle 29'. In a second embodiment the front and rear attachment straps 26 and 25 ending in buckles 29 and 29' are mounted on the holster 13 instead of the spade 24. In this second embodiment the spade 24 is held in the holster 13 by the location of the various other portions of the traction hip brace 5 to the body and friction between the spade 24 and the holster 13 but some positive fastening mechanism, such as screws, bolts or catches, can be used to provide a more positive retention and location. In either embodiment at least one of front groin strap 14 and front attachment strap 26 and one of rear groin strap 14' and rear attachment strap 25 are adjustable. In one variation, both of the front and rear groin straps 14 and 14' are adjustable and front and rear attachment straps 25 and 26 are fixed length. In a second variation the front and rear attachment straps 25 and 26 are adjustable and front and rear groin straps 14 and 14' are fixed length. In a third variation all four straps 14, 14', 25 and 26 are adjustable. In a fourth front groin strap 14 and rear attachment strap 25 are adjustable and rear groin strap 14' and front attachment strap 26 are fixed length. In a fifth variation rear groin strap 14' and front attachment strap 26 are adjustable and front groin strap 14 and rear attachment strap 25 are fixed length. By having at least one of each pair adjustable the traction hip brace 5 can be adjusted as required for the individual.

It is understood that alternate fastener arrangements, such as hook and loop, loops in the straps with hook and loop, D-rings, and the like can be used to fasten the front groin strap 14 and rear groin strap 14' to the spade 24 or the holster 13. It is also understood that the non-brace groin strap 16 may be omitted if desired, as well as the rear groin strap 14' and rear attachment strap 25, depending on materials used and the amount of fixation desired. Further, the rear groin strap 14' can be attached to the saddle harness 10 directly at the front and then passed under the pubic bone as done with front groin strap 14 so that the rear groin strap 14' is not connected to the front groin strap 14. It is also understood that the groin straps 14, 14' and 16 are preferably polypropylene, nylon or polyester but other materials such as leather can be used if desired as is conventional in forming straps.

It is also understood that alternate arrangements can be used to connect the strut member 20 to the saddle harness 10 than the preferred spade 24 and holster 13, such as ending the strut member 20 in a hook shape and securing the hook in the saddle harness 10 or providing a bolted connection between the strut member 20 and the saddle harness 10.

As illustrated in FIG. 2, a lower strut 21 of the strut member 20 attaches to and extends the lateral side 34 of the knee brace 30. The length of the lower strut 21 is adjusted to the individual's hip to knee dimension and secured with threaded fasteners to achieve the desired length. The lower strut 21 has multiple holes and slots 27 to accommodate a range of adjustment. It is understood that alternate methods of allowing adjustment of the length of the lower strut 21 can be used as common in the field of orthopedic braces. The upper end of the strut member 20 contains an articulating hinge mechanism 23 centered near the acetabulofemoral joint and connected to the lower strut 21. The strut hinge 23 is equipped with a locking pin 28 that is used to disable and enable the motion of the strut hinge 23. The motion of the strut hinge 23 is preferably limited to approximately ninety degree of rotation. An upper strut 22 forms the terminus end of the strut member 20 above the strut hinge 23 and is attached to the reinforced spade 24, which forms a connecting element of the strut member 20 to the saddle harness 10. The spade 24 is inserted and secured to the saddle harness 10 in the coupling holster 13. It is from this spade 24 of the strut 20 that downward traction force is applied with adjustment straps 25, 26 to force the femur from the hip socket in one embodiment. In one embodiment the spade 24 end, once removed from the holster 13, can be rotated ninety degrees distal from the centerline of the strut member 20 to serve as a handle to allow the user to apply traction to the femur while sitting. The various portions of the strut member 20 are preferably made from metal to provide a strong base for the application of the various loads. It is understood that other materials or combinations of materials, such as plastics or fiberglass, possibly in combination with metal hinges, can be used as well.

Figure 3:
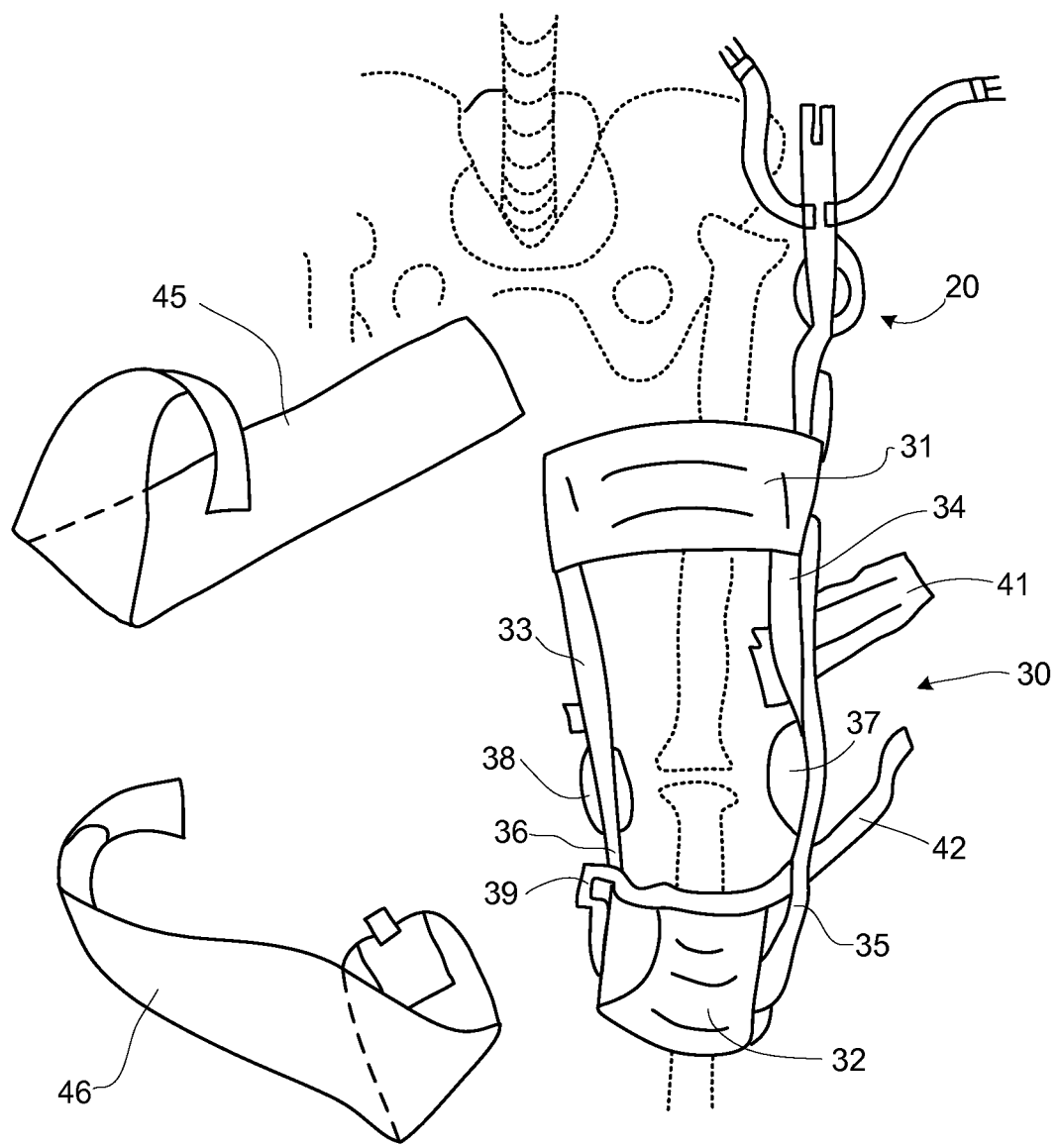
FIG. 3 is a knee brace frontal view of the traction hip brace of FIG. 1.

FIG. 3 shows how the knee and leg are held in semi-rigid type knee brace 30. The knee brace 30 is constructed of lightweight material sufficiently rigid for the loads experienced. Such materials may include steel, aluminum, magnesium or other metal alloy or plastic or reinforced plastics or composites or any combination, as true with the strut member 20. The knee brace 30 is comprised of two shells 31, 32 positioned on the front of the lower thigh just above the knee and just below the knee on the upper shin. The two shells 31, 32 are fitted to the individual's leg and are joined through uprights 33, 34, 35, 36 which pass through two articulating hinge mechanisms 37, 38 on both the lateral and medial sides of the leg. The assembly is preferably fastened together with threaded fasteners where adjustment points are needed and threaded or rivet type fasteners at permanently joined locations, though other fasteners as common with knee braces can be used. The knee brace 30 uprights 33, 34, 35, 36 are fitted with D-ring loops 39 to accept fabric primary straps 41, 42 with hook and loop attachments used to secure the knee brace 30 to the leg. The shells 31, 32; straps 41, 42 and uprights 33, 34, 35, 36 are padded with foam 43, 44 to provide a comfortable fit against the bare skin. The knee brace 30 is secured with the articulating hinge 37, 38 centered in-line with the knee joint and behind the patella. Adjustable secondary elastic straps 45, 46 are secured around the brace at both the lower thigh and below the knee just above the bulge of the gastrocnemius muscle of the lower leg. Secure attachment of the knee brace 30 above the bulge of the gastrocnemius muscle is a positive anchor point on the leg that prevents slippage of the traction hip brace 5 when downward traction is applied to the leg.

The user puts on the saddle harness 10 over undergarment boxers or briefs and tightens the buckle 12 and the groin strap 16. The strut member 20 and knee brace 30 are strapped to the bare leg above and below the knee joint. The strut spade 24 is inserted into the holster 13 of the saddle harness 10. The knee brace primary straps 41, 42 and secondary straps 45, 46, if used, are tightened to affix the knee brace 30 to the leg. The front and rear attachment straps 26, 25 are connected to the front and rear groin straps 14, 14' and the straps 14, 14', 26 and 25 are tensioned to provide traction to the leg and femoral head, pulling it away from the acetabulum in the hip socket.

It is understood that traction hip braces according to the present invention can be used on either leg or hip. Though the illustrated embodiments show left leg and hip use, a mirror image embodiment would be used on the right leg and hip.

A traction hip brace is described that is easy to apply and remove by the user. While wearing the brace the user can continue most daily activities including walking and sitting. The traction hip brace supports the acetabulofemoral joint by pulling the femur head away from the acetabulum socket of the hip joint. The traction applied to the hip joint increases joint space and reduces joint pain and discomfort until joint replacement surgery is ultimately performed.

The above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

I claim:

1. An orthopedic brace comprising:
  a harness for placement about the waist of an individual, said harness including a first groin strap for passing under the pubic bone of the individual on a side of the individual to be placed in traction;
  a knee brace for placement around a knee on the side of the individual to be placed in traction, said knee brace including:

a hinge portion for alignment with the knee joint;
an upper shell connected to said hinge portion for securing about the thigh of the individual; and
a lower shell connected to said hinge portion for securing about the calf of the individual;
a strut member connected to said knee brace and for connection to said harness, said strut member including:
a lower strut connected to said knee brace;
a strut hinge connected to the lower strut and for placement in line with the hip;
a upper strut connected to the strut hinge; and
a harness connecting element connected to said upper strut and for connection to said harness on the side of the harness of the individual to be placed in traction; and
a first attachment mechanism connected to said harness or to said strut member and for connection to said first groin strap, said first attachment mechanism and said first groin strap in combination providing traction to the leg and femoral head of the individual on the side to be placed in traction when said first attachment mechanism is tensioned with said first groin strap.

2. The brace of claim 1, wherein said harness further includes a second groin strap, the brace further comprising:
a second attachment mechanism connected to said harness or to said strut member and for connection to said second groin strap, said second attachment mechanism and said second groin strap in combination providing traction to the leg and femoral head of the individual on the side to be placed in traction when said second attachment mechanism is tensioned with said second groin strap.

3. The brace of claim 2, wherein said first and second attachment mechanisms are connected to said harness.

4. The brace of claim 2, wherein said first and second attachment mechanisms are connected to said strut member.

5. The brace of claim 4, wherein said first and second attachment mechanisms are connected to said harness connecting element.

6. The brace of claim 2, wherein said second groin strap is connected to said first groin strap.

7. The brace of claim 2, wherein said second groin strap is for passing under the pubic bone of the individual on the side of the individual to be placed in traction.

8. The brace of claim 2, wherein said harness includes a third groin strap passing under the pubic bone of the individual on the side of the individual not to be placed in traction.

9. The brace of claim 2, wherein said first and second attachment mechanisms are adjustable straps.

10. The brace of claim 2, wherein said first and second groin straps are adjustable straps.

11. The brace of claim 1, wherein said harness further includes a holster, and wherein said harness connecting element is a spade adapted to mate with said holster.

12. The brace of claim 1, wherein said strut hinge includes a locking mechanism.

13. The brace of claim 1, wherein said first attachment mechanism is connected to said harness.

14. The brace of claim 1, wherein said first attachment mechanism is connected to said strut member.

15. The brace of claim 14, wherein said first attachment mechanism is connected to said harness connecting element.

16. The brace of claim 1, wherein said first attachment mechanism is an adjustable strap.

17. The brace of claim 1, wherein said first groin strap is an adjustable strap.

* * * * *